(12) United States Patent
Jeon et al.

(10) Patent No.: US 7,896,902 B2
(45) Date of Patent: Mar. 1, 2011

(54) MULTI-AXIAL DOUBLE LOCKING BONE SCREW ASSEMBLY

(76) Inventors: Dong Myung Jeon, Draper, UT (US); Patrick Dennis Moore, West Jordan, UT (US)

( * ) Notice: Subject to any disclaimer, the term of this patent is extended or adjusted under 35 U.S.C. 154(b) by 1082 days.

(21) Appl. No.: 11/648,983

(22) Filed: Jan. 3, 2007

(65) Prior Publication Data

US 2007/0270839 A1    Nov. 22, 2007

Related U.S. Application Data

(60) Provisional application No. 60/789,459, filed on Apr. 5, 2006.

(51) Int. Cl.
*A61B 17/70* (2006.01)

(52) U.S. Cl. .................................................. 606/246

(58) Field of Classification Search ................ 606/246, 606/264–272, 274
See application file for complete search history.

(56) References Cited

U.S. PATENT DOCUMENTS

| | | | |
|---|---|---|---|
| 3,741,205 A | 6/1973 | Markolf et al. |
| 4,257,409 A | 3/1981 | Bacal et al. |
| 4,361,141 A | 11/1982 | Tanner |
| 4,369,770 A | 1/1983 | Bacal et al. |
| 4,433,677 A | 2/1984 | Ulrich et al. |
| 4,488,543 A | 12/1984 | Tornier |
| 4,503,848 A | 3/1985 | Caspar et al. |
| 4,573,454 A | 3/1986 | Hoffman |
| 4,611,582 A | 9/1986 | Duff |
| 4,696,290 A | 9/1987 | Steffee |
| 4,763,644 A | 8/1988 | Webb |
| 4,805,602 A | 2/1989 | Puno et al. |
| 4,815,453 A | 3/1989 | Cotrel |
| 4,836,196 A | 6/1989 | Park et al. |
| 4,946,458 A | 8/1990 | Harms et al. |
| 4,955,885 A | 9/1990 | Meyers |
| 4,998,936 A | 3/1991 | Mehdian |

(Continued)

FOREIGN PATENT DOCUMENTS

AU    720999    12/1997

(Continued)

OTHER PUBLICATIONS

S. M. Russell, "Nitinol Melting and Fabrication," SMST-2000 Conference Proceedings, 2001.

*Primary Examiner*—Thomas C Barrett
*Assistant Examiner*—Nicholas Woodall
(74) *Attorney, Agent, or Firm*—Morriss O'Bryant Compagni (57) ABSTRACT

A top-loading multi-axial, double locking bone anchor assembly. A receiver member receives an internal saddle member, a bi-polar member, and a bone anchor through an open bottom, which are retained by an internal threaded ring member threaded onto the receiver member. A double-locking compression retaining member includes an external nut-like fastener and an internal setscrew-like fastener. The nut-like fastener attaches to an upper portion of the receiver member and interfaces with the internal saddle member to retain a desired angular position on the bone anchor and the setscrew-like fastener interfaces with an elongated member placed in a channel of the receiver member to retain it to the assembly. The bone anchor is capable of multi-axial as well as multi-polar positioning with respect to the receiver member.

28 Claims, 9 Drawing Sheets

U.S. PATENT DOCUMENTS

| | | |
|---|---|---|
| 5,002,542 A | 3/1991 | Frigg |
| 5,005,562 A | 4/1991 | Cotrel |
| 5,010,879 A | 4/1991 | Moriya et al. |
| 5,030,220 A | 7/1991 | Howland |
| 5,057,111 A | 10/1991 | Park et al. |
| 5,084,049 A | 1/1992 | Asher et al. |
| 5,092,866 A | 3/1992 | Breard |
| 5,122,131 A | 6/1992 | Tsou |
| 5,133,716 A | 7/1992 | Plaza |
| 5,147,360 A | 9/1992 | Dubousset |
| 5,147,361 A | 9/1992 | Ojima et al. |
| 5,154,718 A | 10/1992 | Cozad et al. |
| 5,176,678 A | 1/1993 | Tsou |
| 5,207,678 A | 5/1993 | Harms et al. |
| 5,217,497 A | 6/1993 | Mehdian |
| 5,222,954 A | 6/1993 | Baker et al. |
| 5,242,445 A | 9/1993 | Ashman |
| 5,246,442 A | 9/1993 | Ashman et al. |
| 5,261,907 A | 11/1993 | Vignaud et al. |
| 5,261,909 A | 11/1993 | Sutterlin et al. |
| 5,261,910 A | 11/1993 | Warden et al. |
| 5,275,600 A | 1/1994 | Allard et al. |
| 5,281,222 A | 1/1994 | Allard et al. |
| 5,282,801 A | 2/1994 | Sherman |
| 5,282,862 A | 2/1994 | Baker et al. |
| 5,306,275 A | 4/1994 | Bryan |
| 5,312,405 A | 5/1994 | Korotko et al. |
| 5,324,290 A | 6/1994 | Zdeblick et al. |
| 5,330,473 A | 7/1994 | Howland |
| 5,334,203 A | 8/1994 | Wagner |
| 5,344,422 A | 9/1994 | Frigg |
| D353,003 S | 11/1994 | Dinello |
| 5,360,431 A | 11/1994 | Puno et al. |
| 5,366,455 A | 11/1994 | Dove et al. |
| 5,395,370 A | 3/1995 | Muller et al. |
| 5,397,363 A | 3/1995 | Gelbard |
| 5,403,316 A | 4/1995 | Ashman |
| 5,423,818 A | 6/1995 | Van Hoeck et al. |
| 5,437,669 A | 8/1995 | Yuan et al. |
| 5,437,670 A | 8/1995 | Sherman et al. |
| 5,437,671 A | 8/1995 | Lozier et al. |
| 5,439,463 A | 8/1995 | Lin |
| 5,443,467 A | 8/1995 | Biedermann et al. |
| 5,466,237 A | 11/1995 | Byrd, III et al. |
| 5,474,551 A | 12/1995 | Finn et al. |
| 5,474,555 A | 12/1995 | Puno et al. |
| 5,474,557 A | 12/1995 | Mai |
| 5,476,462 A | 12/1995 | Allard et al. |
| 5,476,464 A | 12/1995 | Metz-Stavenhagen et al. |
| 5,486,176 A | 1/1996 | Hildebrand et al. |
| 5,487,742 A | 1/1996 | Cotrel |
| 5,496,321 A | 3/1996 | Puno et al. |
| 5,498,263 A | 3/1996 | Dinello et al. |
| 5,501,684 A | 3/1996 | Schlapfer et al. |
| 5,507,746 A | 4/1996 | Lin |
| 5,520,690 A | 5/1996 | Errico et al. |
| 5,522,816 A | 6/1996 | Dinello et al. |
| 5,527,314 A | 6/1996 | Brumfield et al. |
| 5,531,746 A | 7/1996 | Errico et al. |
| 5,531,747 A | 7/1996 | Ray |
| 5,534,002 A | 7/1996 | Brumfield et al. |
| 5,540,689 A | 7/1996 | Sanders et al. |
| 5,549,607 A | 8/1996 | Olson et al. |
| 5,549,608 A | 8/1996 | Errico et al. |
| 5,549,612 A | 8/1996 | Yapp et al. |
| 5,554,157 A | 9/1996 | Errico et al. |
| 5,562,661 A | 10/1996 | Yoshimi et al. |
| 5,562,662 A | 10/1996 | Brumfield et al. |
| 5,569,246 A | 10/1996 | Ojima et al. |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,601,552 A | 2/1997 | Cotrel |
| 5,607,426 A | 3/1997 | Ralph et al. |
| 5,609,593 A | 3/1997 | Errico et al. |
| 5,609,594 A | 3/1997 | Errico et al. |
| 5,616,144 A | 4/1997 | Yapp et al. |
| 5,620,443 A | 4/1997 | Gertzbein et al. |
| 5,620,444 A | 4/1997 | Assaker |
| 5,624,442 A | 4/1997 | Mellinger et al. |
| 5,630,816 A | 5/1997 | Kambin |
| 5,647,873 A | 7/1997 | Errico et al. |
| 5,651,789 A | 7/1997 | Cotrel |
| 5,667,506 A | 9/1997 | Sutterlin |
| 5,667,507 A | 9/1997 | Corin et al. |
| 5,669,910 A | 9/1997 | Korhonene et al. |
| 5,669,911 A | 9/1997 | Errico et al. |
| 5,672,176 A | 9/1997 | Biedermann et al. |
| 5,676,665 A | 10/1997 | Bryan |
| 5,676,666 A | 10/1997 | Oxland et al. |
| 5,681,312 A | 10/1997 | Yuan et al. |
| 5,688,272 A | 11/1997 | Montague et al. |
| 5,688,273 A | 11/1997 | Errico et al. |
| 5,690,630 A | 11/1997 | Errico et al. |
| 5,693,053 A | 12/1997 | Estes |
| 5,704,936 A | 1/1998 | Mazel |
| 5,707,372 A | 1/1998 | Errico et al. |
| 5,709,684 A | 1/1998 | Errico et al. |
| 5,713,904 A | 2/1998 | Errico et al. |
| 5,716,355 A | 2/1998 | Jackson et al. |
| 5,733,285 A | 3/1998 | Errico et al. |
| 5,733,286 A | 3/1998 | Errico et al. |
| 5,752,955 A | 5/1998 | Errico |
| 5,752,957 A | 5/1998 | Ralph et al. |
| 5,776,135 A | 7/1998 | Errico et al. |
| 5,782,833 A | 7/1998 | Haider |
| 5,785,711 A | 7/1998 | Errico et al. |
| 5,797,911 A | 8/1998 | Sherman et al. |
| 5,810,818 A | 9/1998 | Errico et al. |
| 5,810,819 A | 9/1998 | Errico et al. |
| 5,817,094 A | 10/1998 | Errico et al. |
| 5,879,350 A | 3/1999 | Sherman et al. |
| 5,882,350 A | 3/1999 | Ralph et al. |
| 5,885,284 A | 3/1999 | Errico |
| 5,885,286 A | 3/1999 | Sherman et al. |
| 5,891,145 A | 4/1999 | Morrison et al. |
| 5,899,904 A | 5/1999 | Errico et al. |
| 5,899,905 A | 5/1999 | Errico et al. |
| 5,910,142 A | 6/1999 | Tatar |
| 5,928,231 A | 7/1999 | Klein et al. |
| 5,947,966 A | 9/1999 | Drewry |
| 5,961,518 A | 10/1999 | Errico et al. |
| 5,980,523 A | 11/1999 | Jackson |
| 5,984,923 A | 11/1999 | Breard |
| 5,989,251 A | 11/1999 | Nichols |
| 5,989,254 A | 11/1999 | Katz |
| 5,997,539 A | 12/1999 | Errico et al. |
| 6,016,727 A | 1/2000 | Morgan |
| 6,017,344 A | 1/2000 | Errico et al. |
| 6,017,345 A | 1/2000 | Richelsoph |
| 6,053,917 A | 4/2000 | Sherman et al. |
| 6,063,089 A | 5/2000 | Errico et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,083,226 A | 7/2000 | Fiz |
| 6,096,039 A | 8/2000 | Stoltenberg et al. |
| 6,110,173 A | 8/2000 | Thomas, Jr. |
| 6,113,600 A | 9/2000 | Drummond et al. |
| 6,113,601 A | 9/2000 | Tatar |
| 6,132,430 A | 10/2000 | Wagner |
| 6,136,000 A | 10/2000 | Louis et al. |
| 6,136,003 A | 10/2000 | Hoeck et al. |

| | | |
|---|---|---|
| 6,159,213 A | 12/2000 | Rogozinski |
| 6,171,311 B1 | 1/2001 | Richelsoph |
| 6,217,578 B1 | 4/2001 | Crozet et al. |
| 6,234,705 B1 | 5/2001 | Troxell |
| 6,235,028 B1 | 5/2001 | Brumfield et al. |
| 6,238,396 B1 | 5/2001 | Lombardo |
| 6,248,105 B1 | 6/2001 | Schlapfer et al. |
| 6,261,287 B1 | 7/2001 | Metz-Stavenhagen |
| 6,261,288 B1 | 7/2001 | Jackson |
| 6,264,658 B1 | 7/2001 | Lee et al. |
| 6,267,764 B1 | 7/2001 | Elberg |
| 6,280,442 B1 | 8/2001 | Barker et al. |
| 6,283,967 B1 | 9/2001 | Troxell et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,882 B1 | 10/2001 | Lin et al. |
| 6,302,888 B1 | 10/2001 | Mellinger et al. |
| 6,306,137 B2 | 10/2001 | Troxell |
| 6,325,805 B1 | 12/2001 | Ogilvie et al. |
| 6,328,741 B1 | 12/2001 | Richelsoph |
| 6,329,069 B1 | 12/2001 | Azizi et al. |
| 6,355,038 B1 | 3/2002 | Pisharodi |
| RE37,665 E | 4/2002 | Ralph |
| 6,371,957 B1 | 4/2002 | Amrein et al. |
| 6,402,749 B1 | 6/2002 | Ashman |
| 6,402,751 B1 | 6/2002 | Hoeck et al. |
| 6,413,258 B1 | 7/2002 | Bernhardt, Jr. |
| 6,416,515 B1 | 7/2002 | Wagner |
| 6,422,010 B1 | 7/2002 | Julien |
| 6,432,108 B1 | 8/2002 | Burgess et al. |
| 6,451,021 B1 | 9/2002 | Ralph et al. |
| 6,454,773 B1 | 9/2002 | Sherman et al. |
| 6,471,703 B1 | 10/2002 | Ashman |
| 6,471,705 B1 | 10/2002 | Biedermann et al. |
| 6,485,491 B1 | 11/2002 | Farris et al. |
| 6,488,681 B2 | 12/2002 | Martin et al. |
| 6,524,310 B1 | 2/2003 | Lombardo et al. |
| 6,537,276 B2 | 3/2003 | Metz-Stavenhagen |
| 6,551,318 B1 | 4/2003 | Stahurski |
| 6,551,323 B2 | 4/2003 | Doubler et al. |
| 6,554,832 B2 | 4/2003 | Shluzas |
| 6,554,834 B1 | 4/2003 | Crozet et al. |
| 6,562,040 B1 | 5/2003 | Wagner |
| 6,565,565 B1 | 5/2003 | Yuan et al. |
| 6,565,567 B1 | 5/2003 | Haider |
| 6,585,740 B2 | 7/2003 | Schlapfer et al. |
| 6,589,243 B1 | 7/2003 | Viart et al. |
| 6,602,253 B2 | 8/2003 | Richelsoph et al. |
| 6,602,254 B2 | 8/2003 | Gertzbein et al. |
| 6,616,668 B2 | 9/2003 | Altarac et al. |
| 6,616,669 B2 | 9/2003 | Ogilvie et al. |
| 6,626,904 B1 | 9/2003 | Jammet et al. |
| 6,626,908 B2 | 9/2003 | Cooper et al. |
| 6,626,909 B2 | 9/2003 | Chin |
| 6,660,004 B2 | 12/2003 | Barker et al. |
| 6,673,073 B1 | 1/2004 | Schafer |
| 6,676,661 B1 | 1/2004 | Martin Benlloch et al. |
| 6,689,133 B2 | 2/2004 | Morrison et al. |
| 6,716,214 B1 | 4/2004 | Jackson |
| 6,723,100 B2 | 4/2004 | Biedermann et al. |
| 6,733,502 B2 | 5/2004 | Altarac et al. |
| 6,736,817 B2 | 5/2004 | Troxell et al. |
| 6,740,086 B2 | 5/2004 | Richelsoph |
| 6,755,830 B2 | 6/2004 | Minfelde et al. |
| 6,773,437 B2 | 8/2004 | Ogilvie et al. |
| 6,780,186 B2 | 8/2004 | Errico et al. |
| 6,783,530 B1 | 8/2004 | Levy |
| 6,827,719 B2 | 12/2004 | Ralph et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,030 B2 | 2/2005 | Martin et al. |

| | | | |
|---|---|---|---|
| 6,869,433 B2 | 3/2005 | Glascott | |
| 6,896,677 B1 | 5/2005 | Lin | |
| 6,974,460 B2 | 12/2005 | Carbone et al. | |
| 7,018,378 B2 | 3/2006 | Biedermann et al. | |
| 7,022,122 B2 | 4/2006 | Amrein et al. | |
| 7,087,057 B2 | 8/2006 | Konieczynski et al. | |
| 7,137,985 B2 | 11/2006 | Jahng | |
| 7,322,981 B2 | 1/2008 | Jackson | |
| 7,335,202 B2 | 2/2008 | Matthis et al. | |
| 7,445,627 B2 * | 11/2008 | Hawkes et al. | 606/269 |
| 7,476,239 B2 * | 1/2009 | Jackson | 606/266 |
| 7,503,924 B2 * | 3/2009 | Lee et al. | 606/272 |
| 7,530,992 B2 * | 5/2009 | Biedermann et al. | 606/272 |
| 7,591,839 B2 * | 9/2009 | Biedermann et al. | 606/266 |
| 2001/0047171 A1 | 11/2001 | Troxell et al. | |
| 2002/0035366 A1 | 3/2002 | Walder et al. | |
| 2002/0045896 A1 | 4/2002 | Michelson | |
| 2002/0052603 A1 | 5/2002 | Nichols et al. | |
| 2002/0082599 A1 | 6/2002 | Crandall et al. | |
| 2002/0138077 A1 | 9/2002 | Ferree | |
| 2002/0143327 A1 | 10/2002 | Shluzas | |
| 2002/0169448 A1 | 11/2002 | Vanacker | |
| 2002/0169450 A1 | 11/2002 | Lange | |
| 2002/0169451 A1 | 11/2002 | Yeh | |
| 2002/0193794 A1 | 12/2002 | Taylor | |
| 2003/0004511 A1 | 1/2003 | Feree | |
| 2003/0004512 A1 | 1/2003 | Farris et al. | |
| 2003/0028192 A1 | 2/2003 | Schar et al. | |
| 2003/0045874 A1 | 3/2003 | Thomas, Jr. | |
| 2003/0050640 A1 | 3/2003 | Lee et al. | |
| 2003/0083659 A1 | 5/2003 | Lin et al. | |
| 2003/0105460 A1 | 6/2003 | Crandall et al. | |
| 2003/0125741 A1 | 7/2003 | Biedermann et al. | |
| 2003/0149431 A1 | 8/2003 | Varieur | |
| 2003/0176862 A1 | 9/2003 | Taylor et al. | |
| 2003/0191473 A1 | 10/2003 | Taylor | |
| 2004/0002710 A1 | 1/2004 | Han et al. | |
| 2004/0122425 A1 | 6/2004 | Suzuki et al. | |
| 2004/0138662 A1 | 7/2004 | Landry et al. | |
| 2004/0153068 A1 | 8/2004 | Janowski et al. | |
| 2004/0186474 A1 | 9/2004 | Matthis et al. | |
| 2004/0236330 A1 | 11/2004 | Purcell et al. | |
| 2004/0259085 A1 | 12/2004 | Chang | |
| 2004/0267264 A1 | 12/2004 | Konieczynski et al. | |
| 2005/0177154 A1 | 8/2005 | Moumene et al. | |
| 2005/0187548 A1 | 8/2005 | Butler et al. | |
| 2005/0192571 A1 | 9/2005 | Abdelgany | |
| 2005/0203516 A1 * | 9/2005 | Biedermann et al. | 606/61 |
| 2005/0261687 A1 | 11/2005 | Garamszegi et al. | |
| 2005/0267472 A1 | 12/2005 | Biedermann et al. | |
| 2005/0277928 A1 * | 12/2005 | Boschert | 606/61 |
| 2006/0058788 A1 | 3/2006 | Hammer et al. | |
| 2006/0064090 A1 | 3/2006 | Park | |
| 2006/0100626 A1 | 5/2006 | Rathbun et al. | |
| 2007/0016193 A1 | 1/2007 | Ritland | |
| 2007/0049937 A1 | 3/2007 | Matthis et al. | |
| 2007/0088358 A1 | 4/2007 | Yuan et al. | |
| 2007/0173833 A1 | 7/2007 | Butler et al. | |
| 2007/0225710 A1 | 9/2007 | Jahng et al. | |
| 2007/0233087 A1 | 10/2007 | Schlapfer | |
| 2007/0270839 A1 | 11/2007 | Jeon et al. | |
| 2007/0276380 A1 | 11/2007 | Jahng et al. | |

FOREIGN PATENT DOCUMENTS

| | | |
|---|---|---|
| DE | 3219575 | 12/1983 |
| DE | 3711013 | 6/1988 |
| DE | 4330837 | 3/1995 |
| DE | 19509332 | 8/1996 |
| EP | 0669109 A1 | 8/1995 |
| EP | 0813845 | 6/1996 |
| EP | 0811357 | 12/1997 |
| EP | 0953316 | 11/1999 |

| | | | | | | |
|---|---|---|---|---|---|---|
| FR | 2645427 | 4/1989 | | GB | 2173104 A | 10/1986 |
| FR | 2689750 A | 10/1993 | | JP | 2002-355252 | 12/2002 |
| FR | 2714590 | 1/1994 | | WO | WO 02/38061 | 11/2001 |
| GB | 2173104 | 10/1986 | | | | |

\* cited by examiner

MULTI-AXIAL DOUBLE LOCKING BONE SCREW ASSEMBLY

CROSS-REFERENCE TO RELATED APPLICATIONS

This application claims the benefit of U.S. Provisional Application No. 60/789,459, filed Apr. 5, 2006, the disclosure of which is incorporated herein by reference in its entirety.

TECHNICAL FIELD

The present invention relates to devices and implants used in osteosynthesis and other orthopedic surgical procedures such as devices for use in spinal surgery, and, in particular, to an posterior pedicle screw, connector/rod assembly which is implantable within a patient for stabilization of the spine. Specifically, the present invention relates to a top loading bone anchor assembly capable of achieving multiple angular axial orientations with respect to an elongated member extending along bone tissue.

BACKGROUND

Several techniques and systems have been developed for correcting and stabilizing damage or malformation of bones, especially the long bones and the spine. In one type of system, an elongated member such as a bendable rod is disposed longitudinally along a length of the bone(s). In spinal applications, the rod is preferably bent to correspond to the normal curvature of the spine in the particular region being instrumented. For example, the rod can be bent to form a normal kyphotic curvature for the thoracic region of the spine, or a lordotic curvature for the lumbar region. In accordance with such a system, the rod is engaged to various vertebrae along a length of the spinal column by way of a number of fixation elements. A variety of fixation elements can be provided which are configured to engage specific portions of the vertebra and other bones. For instance, one such fixation element is a hook which is configured to engage the laminae of the vertebra. Another very prevalent fixation element is a screw that can be threaded into various parts of the vertebrae or other bones.

In one typical spinal procedure utilizing a bendable rod, the rod is situated on opposite sides of the spine or spinous processes. A plurality of bone screws are threaded into a portion of several vertebral bodies, very frequently into the pedicles of these vertebrae. The rods are affixed to this plurality of bone screws to apply corrective and stabilizing forces to the spine.

One example of a rod-type spinal fixation system includes elongated rods and a variety of hooks, screws, and bolts, all configured to create a segmental construct throughout the spine. In one aspect of the system, the spinal rod is connected to the various vertebral fixation elements using eyebolts. In this configuration, the fixation elements are engaged to the spinal rod laterally adjacent to the rod. In another aspect of the system, a variable angle screw may be engaged to the spinal rod with an eyebolt. The variable angle screw allows pivoting of the bone screw in a single plane parallel to the plane of the spinal rod. Details of this type of system can be found in U.S. Pat. No. 5,261,909 to Sutterlin et al., the disclosure of which is incorporated by reference herein. This type of system allows a surgeon to apply vertebral fixation elements, such as a spinal hook or a bone screw, to the spine in appropriate anatomic positions and also allows the surgeon to easily engage a bent spinal rod to each of the fixation elements for final tightening.

Another rod-type fixation system provides a variety of fixation elements for engagement between an elongated rod and the spine. In one aspect of the system, the fixation elements themselves include a body that defines a slot within which the spinal rod is received. The slot includes a threaded bore into which a threaded plug is engaged to clamp the rod within the body of the fixation element. The system uses hooks and bone screws having this "open-back" configuration. Details of this type of system can be found in U.S. Pat. No. 5,005,562, the disclosure of which is incorporated by reference herein.

The fixation elements of these types of systems are capable only of pivoting about the spinal rod to achieve variable angular positions relative to the rod. While this limited range of relative angular positioning may be acceptable for many spinal pathologies, many other cases require more creative orientation of a fixation element (such as a bone screw relative) to a spinal rod. While certain aspects of this problem may be addressed by the variable angle screw of the '909 patent type of system, there remains a need for a bone screw capable of angular orientation in multiple planes relative to the spinal rod, as well as multiple spherical head orientations. Preferably, the bone screw axis is capable of various three dimensional orientations with respect to the spinal rod. Screws of this type of angular orientation in multiple planes relative to the spinal rod have been referred to as poly-axial or multi-axial bone screws. The use of both angular orientations in multiple planes relative to the spinal rod allows for virtually unlimited axial angulations of the bone engaging screw member within the design parameters as well as an ultra-low profile of the said device utilizing a minimum of components without sacrificing the security of the interfaces of the invention components.

Others have approached the solution to this problem with various poly-axial screw designs. For example, U.S. Pat. No. 5,466,237 to Byrd et al., the disclosure of which is incorporated by reference herein, describes a bone screw which includes a spherical projection on the top of the bone screw. An externally threaded receiver member supports the bone screw and a spinal rod on top of the spherical projection. An outer nut is tightened onto the receiver member to press the spinal rod against the spherical projection to accommodate various angular orientations of the bone screw relative to the rod. While this particular approach utilizes a minimum of components, the security of the fixation of the bone screw to the rod is lacking. In other words, the engagement or fixation between the small spherical projection on the bone screw and the spinal rod is readily disrupted when the instrumentation is subjected to the high loads of the spine, particularly in the lumbar region.

Another approach is shown in U.S. Pat. No. 4,946,458 to Harms et al., the disclosure of which is incorporated by reference herein. A spherical headed bone screw is supported within separate halves of a receiver member. The bottoms of the halves are held together by a retaining ring. The top of the receiver halves are compressed about the bone screw by nuts threaded onto a threaded spinal rod. In another approach taken by Harms et al., in U.S. Pat. No. 5,207,678, the disclosure of which is incorporated by reference herein, a receiver member is flexibly connected about a partially spherical head of a bone screw. Conical nuts on opposite sides of the receiver member are threaded onto a threaded rod passing through the receiver. As the conical nuts are threaded toward each other, the receiver member flexibly compresses around the head of the bone screw to clamp the bone screw in its variable angular position. One detriment of the systems in the two Harms et al. patents is that the spinal rod must be threaded in order to accept the compression nuts. It is known that threading rods can tend to weaken the rods in the face of severe spinal loads. Moreover, the design of the bone screws in these patents requires a multiplicity of parts, which makes it fairly complicated to achieve complete fixation of the bone screw.

A further approach is illustrated in U.S. Pat. No. 5,797,911 to Sherman et al., the disclosure of which is incorporated by reference herein. A U-shaped holder is provided, through the top of which a bone fastener topped with a crown member is loaded. The holder accommodates a rod in a channel above the crown member and a compression member above the rod. The compression member presses on the rod and crown member to lock the fastener against the holder in any of a number of angles in three dimensions with respect to the rod. This approach has proven to be quite effective in addressing the above-identified problems. However, it does not permit bottom-loading of the fastener. Additionally, the holder is somewhat bulky in order to accommodate the other structural components.

Yet a further approach is shown in U.S. Pat. No. 5,733,285 to Errico et al., the disclosure of which is incorporated by reference herein. In this system, a holder is provided with a tapered and colletted portion at the bottom into which a bone fastener head is inserted. A sleeve is provided that slides down around the colletted portion to crush lock the colletted portion around the head of the bone fastener. This apparatus is believed to be relatively bulky and difficult to manipulate given the external sliding locking mechanism. It is further dependent on the fit of the external sleeve and the relative strength of the collet and its bending and crushing portions for secure locking of the bone fastener head.

There is therefore a need remaining in the industry for an ultra-low profile, multi-axial/double-locking bone anchor that can be readily and securely engaged to an elongated member of any configuration—i.e., smooth, roughened, knurled or even threaded—which achieves greatly improved angulations of the bone anchor, improved strength, and reduced size, including profile and bulk, of the components used to engage the bone anchor to the elongated member in any of a variety of angular orientations.

SUMMARY

In one illustrative embodiment, the present invention includes a top-loading multi-axial, double locking bone anchor system or assembly. A receiver member receives an internal saddle member, a bi-polar member, and a bone anchor through an open bottom, which are retained by an internal threaded ring member threaded onto the receiver member. A double-locking compression retaining member includes an external nut-like fastener and an internal setscrew-like fastener. The nut-like fastener attaches to an upper portion of the receiver member and interfaces with the internal saddle member to retain a desired angular position on the bone anchor and the setscrew-like fastener interfaces with an elongated member placed in a channel of the receiver member to retain it to the assembly. The apposing forces created by these fasteners create a locking force within the double-locking compression retaining member thus reducing the likelihood of involuntary loosening of the double-locking compression retainer member. The bone anchor is capable of multi-axial as well as multi-polar positioning with respect to the receiver member.

Additional embodiments, examples, advantages, and objects of the present invention will be apparent to those of ordinary skill in the art from the following specification.

DESCRIPTION OF THE DRAWINGS

It will be appreciated by those of ordinary skill in the art that the elements depicted in the various drawings are not to scale, but are for illustrative purposes only. The nature of the present invention, as well as other embodiments of the present invention may be more clearly understood by reference to the following detailed description of the invention, to the appended claims, and to the several drawings attached hereto.

FIG. 3a is a side elevational view of an embodiment of the receiver member of the assembly illustrated in FIGS. 1 and 2.

FIG. 3b is a front elevational view of the embodiment of the receiver member illustrated in FIG. 3a.

FIG. 3c is a sectional view, taken along the line 3c-3c in FIG. 3a, and viewed in the direction of the arrows, of the embodiment of the receiver member illustrated in FIG. 3a.

FIG. 3d is a sectional view, taken along the lines 3d-3d of FIG. 3b and viewed in the direction of the arrows, of the embodiment of the receiver member illustrated in FIG. 3a.

FIG. 4b is a sectional view, taken along the lines 4b-4b of FIG. 4a and viewed in the direction of the arrows, of the embodiment of the bone anchor illustrated in FIG. 4a.

FIG. 4c is a magnified view of one embodiment of the head of the bone anchor illustrated in FIG. 4a.

FIG. 5b is a front view of the embodiment of an internal saddle member illustrated in FIG. 5a.

FIG. 5c is a sectional view, taken along the lines 5c-5c in FIG. 5a and viewed in the direction of the arrows, of the embodiment of the internal saddle member illustrated in FIG. 5a.

FIG. 5d is a sectional view, taken along the lines 5d-5d in FIG. 5b and viewed in the direction of the arrows, of the embodiment of the internal saddle member illustrated in FIG. 5a.

FIG. 6b is a sectional view, taken along the lines of 6b-6b in FIG. 6a and viewed in the direction of the arrows, of the embodiment of the internal threaded ring member illustrated in FIG. 6a.

FIG. 7a is a top view of one embodiment of a retaining member used in the assembly illustrated in FIGS. 1 and 2.

FIG. 7b is a side elevational view of the retaining member illustrated in FIG. 7a.

FIG. 7c is a bottom view of the retaining member illustrated in FIG. 7a.

FIG. 7d is a sectional view of the retaining member illustrated in FIG. 7a, taken along the lines 7d-7d in FIG. 7a and viewed in the direction of the arrows.

FIG. 8b is a sectional view, taken along the line 8b-8b in FIG. 8a and viewed in the direction of the arrows, of the bi-polar member illustrated in FIG. 8a.

DETAILED DESCRIPTION

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Figure 1:
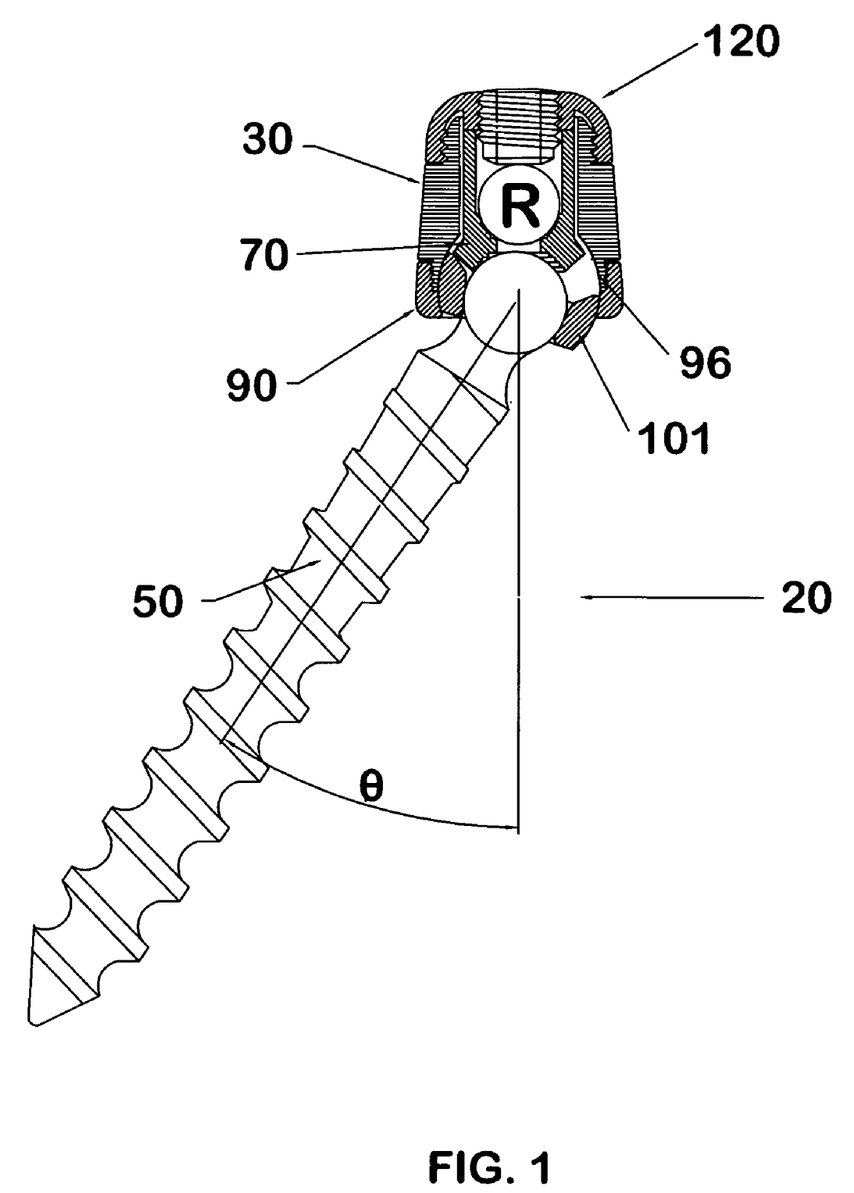
FIG. 1 is a partial sectional side elevational view of one illustrative embodiment of the multi-axial, double-locking bone screw anchor assembly in accordance with the present invention.
Figure 2:
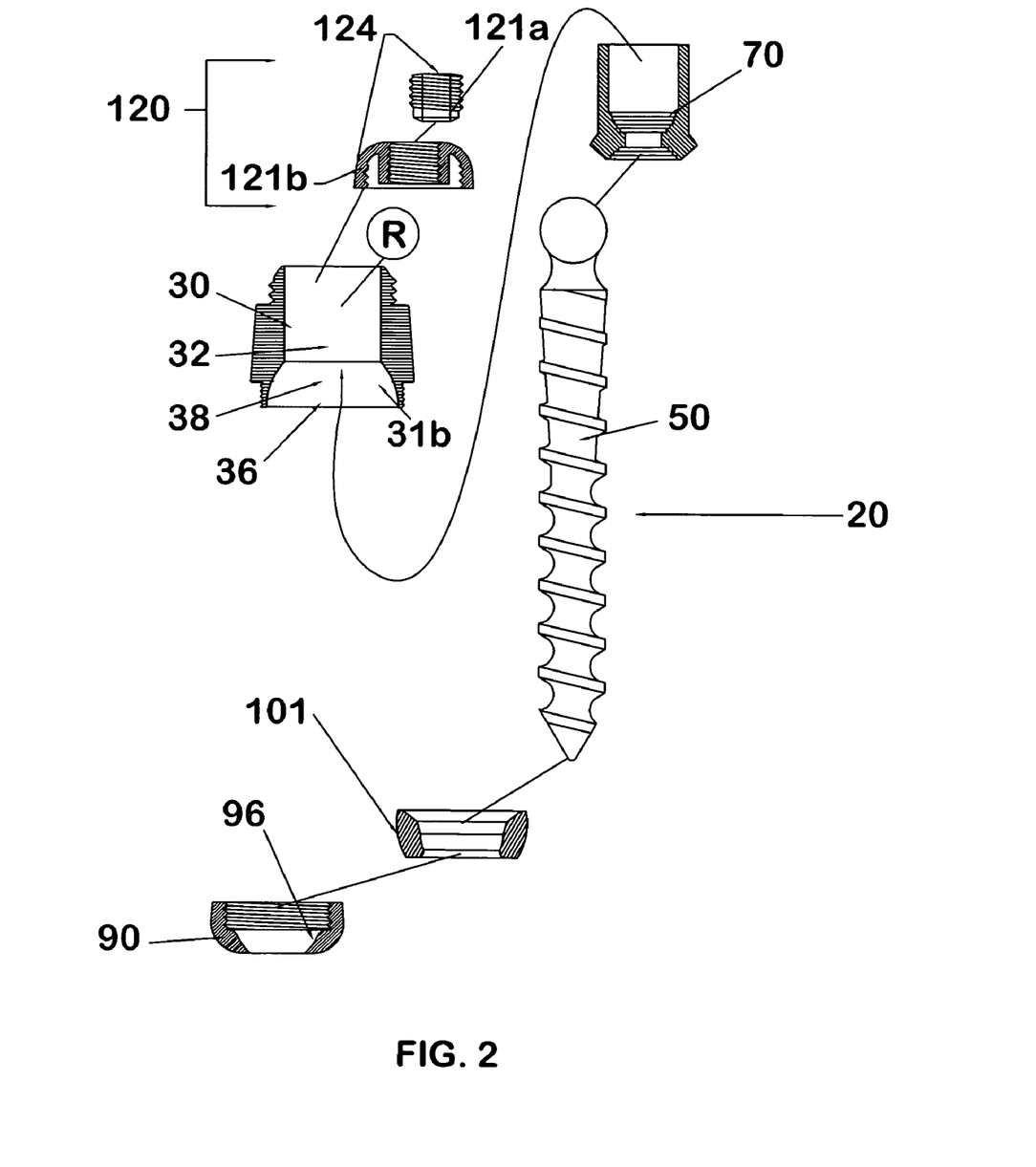
FIG. 2 is an exploded partial sectional view of the assembly depicted in FIG. 1.

Referring generally to FIGS. 1 and 2, there is shown one illustrative embodiment of a multi-axial/double-locking bone anchor assembly 20 in accordance with the principles of the present invention. In the illustrated embodiment, assembly 20 includes a receiver member 30, a bone anchor 50, an internal saddle member 70, a bi-polar member 101, an internal threaded ring member 90, and a retainer assembly 120. The assembly 20 of the present invention is designed for use with an elongated member R, such as a spinal rod, bar or other orthopedic construct.

Referring now generally to FIGS. 3a-3d, one embodiment of the receiver member 30 depicted in FIGS. 1 and 2 is shown in more detail. Receiver member 30 is a generally circular member having at least one sidewall 37 surrounding a central aperture 32. Sidewall 33 defines an upper portion 31a and a lower portion 31b of the receiver 30. Central aperture 32 extends through receiver member 30 from an upper aperture 33 in top end 34 of upper portion 31a to a lower aperture 35 in bottom end 36 of lower portion 31b. Central aperture 32 may include, in one specific embodiment, a chamber/void 38 defined by a chamber wall 39 in lower portion of receiver 30. The diameter of the central aperture 32 at chamber/void 38 is larger than the diameter of the central aperture 32 in upper portion 31a. It will be appreciated that in other embodiments, the upper and lower portions 31a, 31b can have a variety of configurations, such as each having one or more sections of differing diameter.

Figures 3A, 3B:
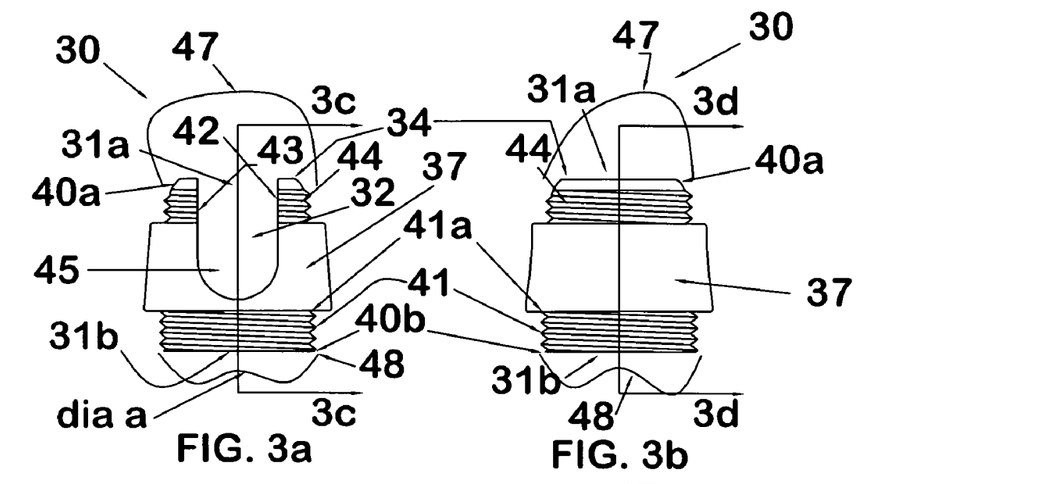
Figures 3C, 3D:
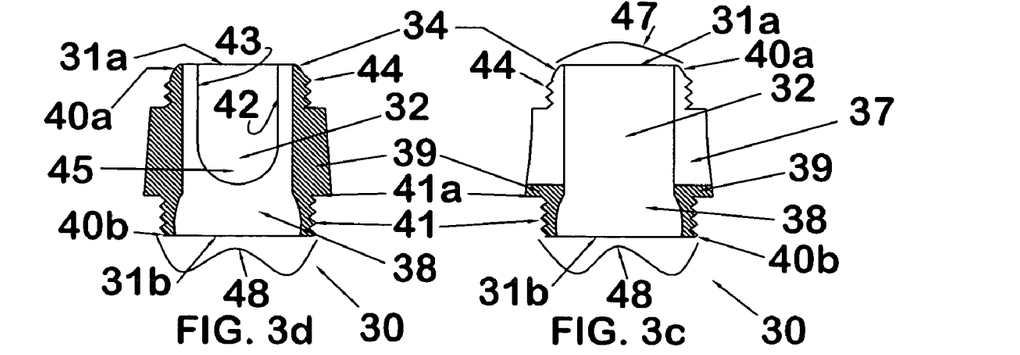

Receiver member 30 may have a chamfered or rounded edge 40a at top end 34, and may have a surrounding chamfered or rounded edge 40b at the bottom end 36. Proximate to bottom end 36, the exterior surface of the receive member 30 may include threads 41 and an associated ledge 41a around sidewall 37. In the illustrated embodiment, threads 41 extend around the entire perimeter of lower surface 32, although it will be appreciated that threads 41 could extend only partially around the perimeter of lower surface 32. Thread 41 has a thread depth A (FIG. 9) and a thread diameter B (FIG. 3a).

Figure 9:
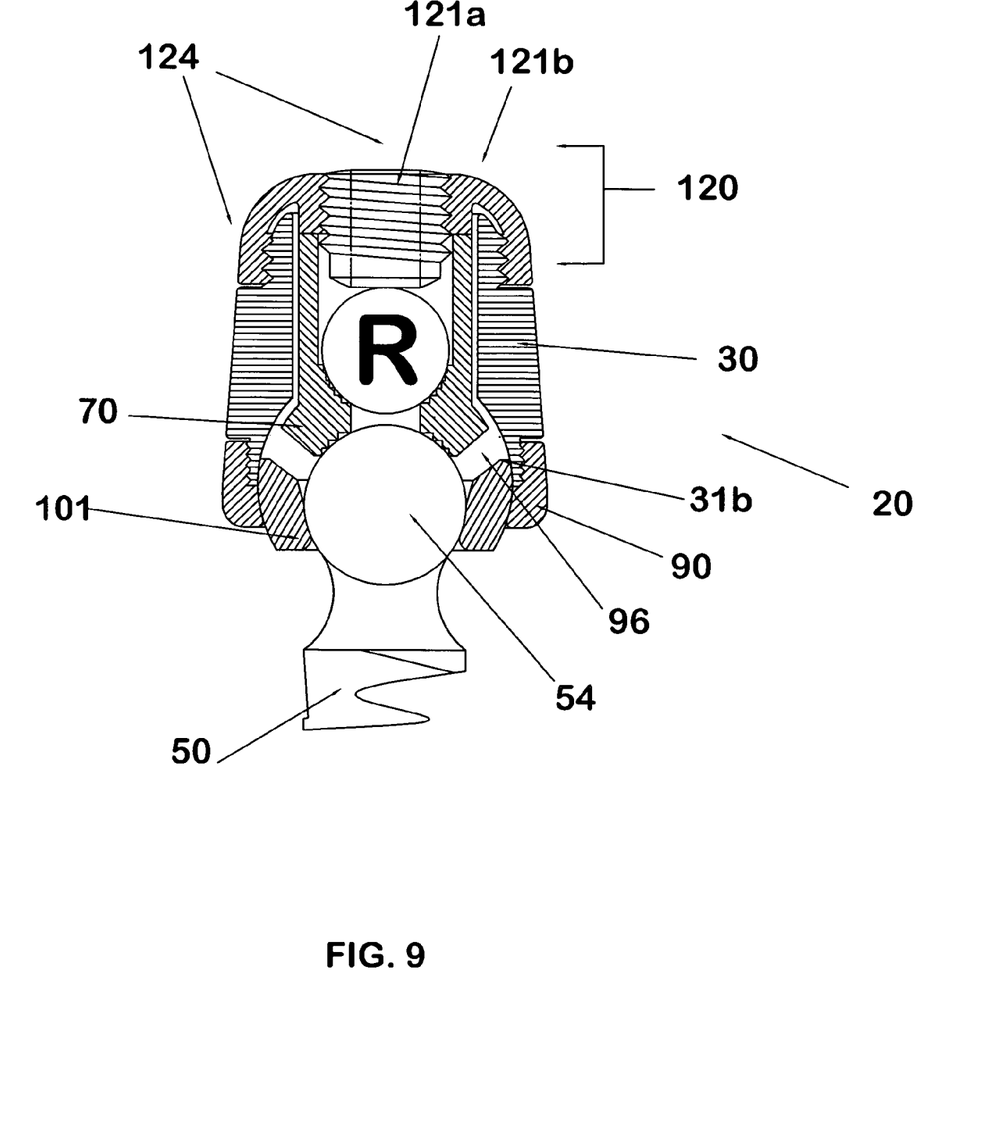
FIG. 9 is an enlarged sectional view of the assembly illustrated in FIGS. 1 and 2.

Receiver member 30 may include one or more pairs of upright branches 42, 43 in upper portion 31a, through which central aperture 32 extends. Branches 42, 43 may further define a generally U-shaped channel 45 transverse to opening 32 that communicates with upper portion 31a and lower portion 31b of opening 32, and that accommodates an elongated member R (FIG. 9). In one specific embodiment, external threads 44 are formed in branches 42, 43, and may be a modified acme buttress thread. The width 47 of upper portion 31a of receiver member 30 (which includes branches 42, 43) may be narrower than the width 48 of bottom portion 31b of receiver member 30, thereby reducing the bulk and profile of receiver member 30.

Figure 4A:
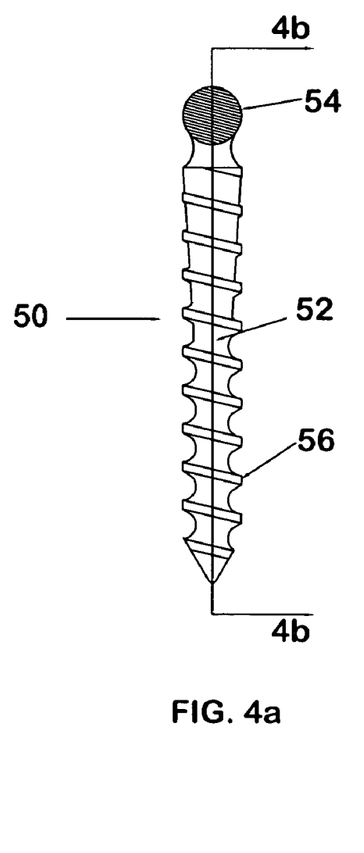
FIG. 4a is a side elevational view of an embodiment of a bone anchor used in the assembly illustrated in FIGS. 1 and 2.
Figures 4B, 4C:
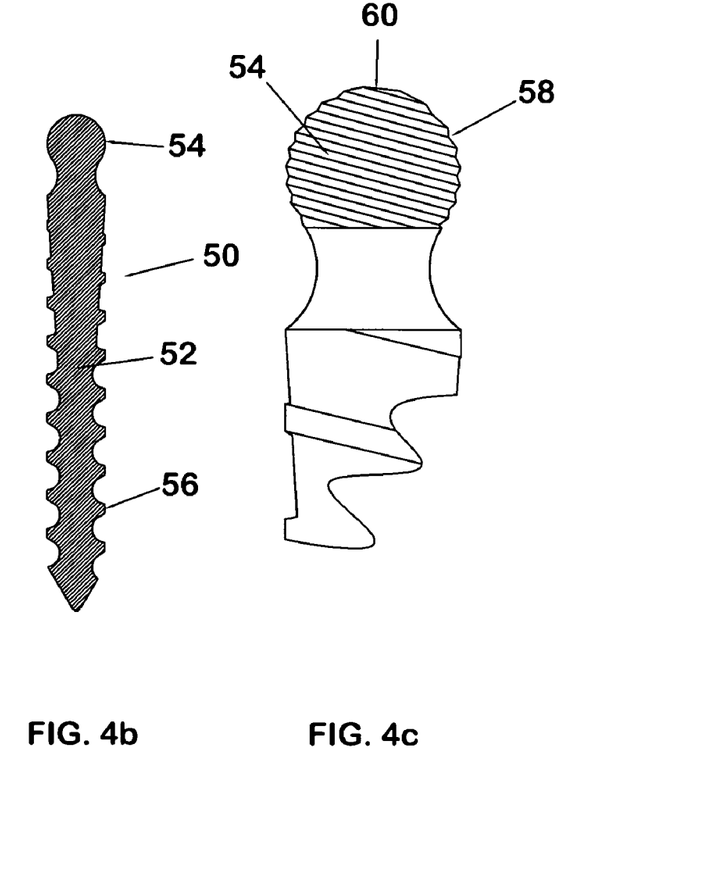
Figure 5A:
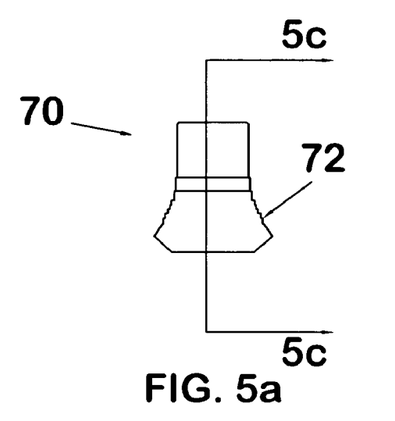
FIG. 5a is a side view of one embodiment of an internal saddle member which may be used in the assembly illustrated in FIGS. 1 and 2.
Figure 5B:
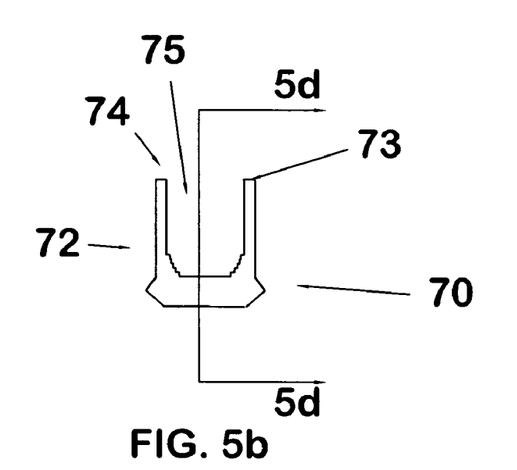
Figure 5C:
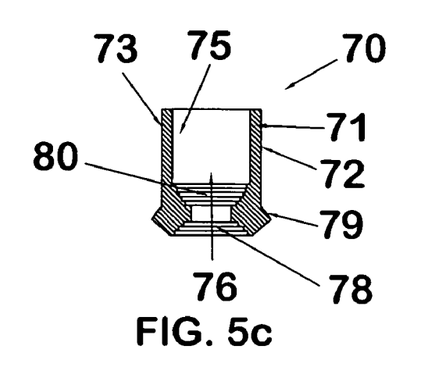
Figure 5D:
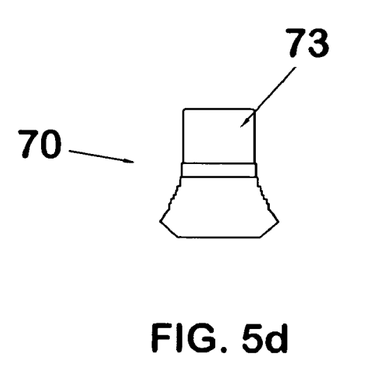

Referring now generally to FIGS. 4a-4c, one illustrative embodiment of a bone anchor 50 which may be used with systems in accordance with the present invention is illustrated. The illustrated bone anchor 50 is a bone screw. Bone anchor 50 includes an anchorage portion 52 and a head portion 54. As illustrated, anchorage portion 52 includes at least one thread 56, which may be a cancellous self-tapping thread, around an elongated shaft. Head portion 54 is disposed at a proximal end of the shaft and has a curvate cross-sectional shape. As illustrated, this curvate shape may form a portion of a sphere, though alternative curvate and other configurations may be employed. Head 54 may include structures for improving purchase with the surrounding members of system 20. For example, head 54 may feature a series of ridges 58 for improving purchase with the lower inside of internal saddle member 70 (described below), or may have alternative friction-increasing surface configurations, such as roughening or knurling. Further, head 54 may include a tool-engaging print 60 (not shown) with which a tool (not shown) may be engaged to drive anchorage portion 52 into a bone. Tool-engaging print 60 may be an interior print or an exterior print, and it may have any of a number of configurations, such as hexagonal, hexalobate, X-shaped, or other known torque-transferring configurations.

Other embodiments of bone anchor 50 with a suitable head 54 may be used in systems in accordance with the principles of the present invention. For example, bone anchor 50 could be a bone-engaging hook rather than a screw. In such an embodiment, anchorage portion 52 would be configured with a hook rather than an elongated section with thread 56.

Head 54 of bone anchor 50 may be shaped and sized to fit within at least interior portion 78 of internal saddle member 70 (FIG. 1 and FIGS. 5a-5d) and chamber 38 of receiver member 30. Specifically, head 54 may have a width that is smaller than the width of lower aperture 35 and chamber 38 of receiver member 30. As more fully described below, bone anchor 50 may be inserted into receiver member 30, with anchorage portion 50 entering through opening 80 and interfacing with surface 78 of internal saddle member 70 or 70A.

Referring now to FIGS. 5a-5d, there is depicted one illustrative embodiment of an internal saddle member 70 in accordance with the principles of the present invention. Internal saddle member 70 may be generally shaped as a hollow cylinder, having an exterior surface 72 with a beveled top edge 74 surrounding a central channel 76 which runs from top edge 74 to a bottom opening. The central channel 76 includes an enlarged portion 77 sized to retain at least a portion of head 54 of a bone anchor 50 near the bottom opening. The enlarged portion 77 may taper from a narrower top to a wider bottom near the bottom opening, generally mirroring the portion of the head 54 of bone anchor 50. For example, the illustrated embodiment of enlarged portion 77 has the shape of part of a sphere. The interior surface 78 of enlarged portion 77 may be provided with a friction or purchase enhancing surface configuration for cooperation with head 54 of bone anchor 50. As depicted, the interior surface 78 has ridges or steps 80 in the enlarged portion 77. In other embodiments, the surface 78 may be roughened or knurled.

In the illustrated embodiment of internal saddle member 70, a screw driving tool can access the bone anchor 50 through central channel 76, in order to drive the bone anchor 50. Internal saddle member 70 is sized and shaped to fit receiver member 30 by loading through lower aperture 35 and chamber 38. The outer dimension of the lower portion of internal saddle member 70 may be slightly smaller than the inner dimension of chamber 38 so the saddle member 70 is slidably movable within chamber 38 and opening 32. Further, in the illustrated embodiment the outer dimension of the lower potion of the internal saddle member 70 is larger than the inner dimension of central aperture 32 in the upper portion 31a, so that internal saddle member 70 cannot move into upper portion 31a. As depicted, this may be accomplished by an external shelf 79 on the outer surface of the lower portion of saddle member 70.

In the upper portion of saddle member 70, sidewall 71 defines two or more pairs of branches 72 and 73, through which central channel 76 extends. Branches 72, 73 may further define one or more generally U-shaped transverse channels 75, which run generally perpendicularly to central channel 76 to accommodate an elongated member R (FIG. 9). Upon assembly, transverse channel 75 may align with U-shaped channel 45 to allow for the top loading of the elongated member R. The interior surface of the transverse channel 75 may be provided with a friction or purchase enhancing surface configuration for cooperation with an elongated member R. As depicted, the interior surface of transverse channel 75 may have ridges or steps, or it may be roughened or knurled.

Figure 8A:
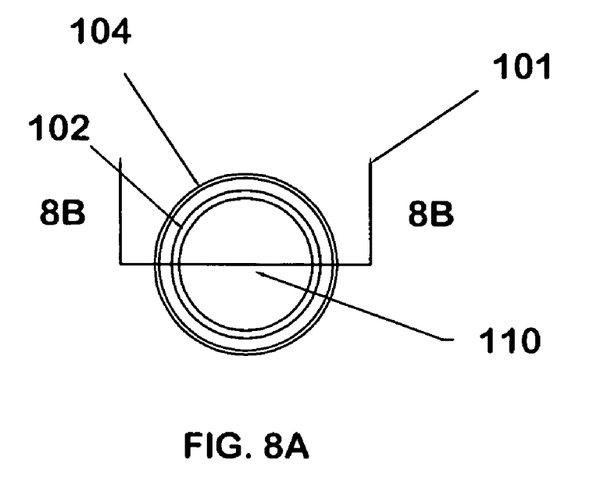
FIG. 8a is a top view of one embodiment of a bi-polar member used in the assembly illustrated in FIGS. 1 and 2.
Figure 8B:
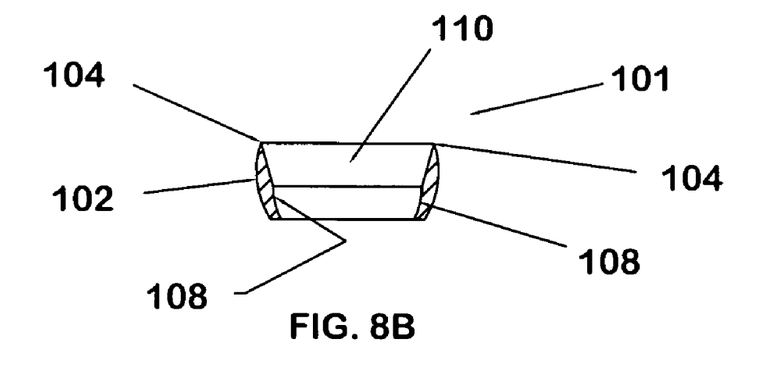
Figure 8C:
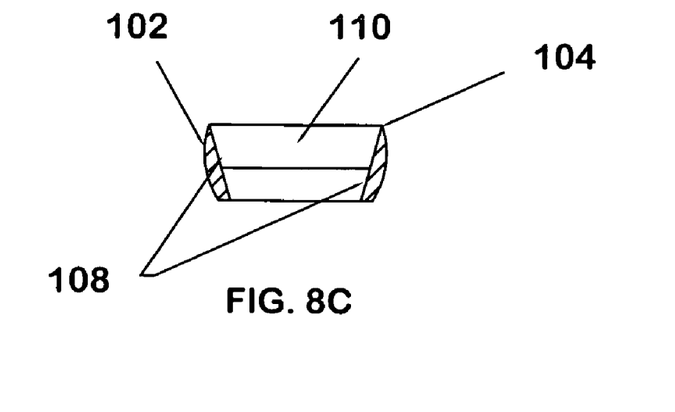
FIG. 8c is a sectional view substantially similar to FIG. 8b of another embodiment of a bi-polar member which may be used with assemblies in accordance with the present invention.

Referring now to FIGS. 8A-8C, there is shown one illustrative embodiment of bi-polar member 101 in accordance with the principles of the present invention. In the depicted embodiment, bi-polar member 101 is formed as a circular disc, having an exterior surface 102 with a top edge 104 and an interior surface 108. Interior surface 108 is configured to accommodate head 54 of bone anchor 50. Accordingly, the illustrated embodiment of interior surface 108 in FIGS. 8A and 8B has the shape of part of a sphere. It will be appreciated that in other embodiments, the shape may differ, in order to accommodate other head 54 shapes. For example, see the conical interior surface 108' of FIG. 8C. Interior surface 108 can be provided with a friction or purchase-enhancing surface configuration (e.g. roughening or knurling) for cooperation with head 54 of bone anchor 50.

Bi-polar member 101 also includes a hole 110 faced by interior surface 108. Hole 110 is provided so that bone anchor 50 may be partially passed therethrough, allowing the bone engaging threads 56 of bone anchor 50 to be available through bi-polar member 101, while head 54 is retained therein. The dimension of hole 110 of the bi-polar member 101 is preferably slightly larger than the outer dimension of bone anchor head 54 so that the bone anchor head 54 is slidably and rotatably movable within hole 110 and bipolar member 101.

Bi-polar member 101 is sized and shaped to fit within at least lower portion 31b of central aperture 32 and chamber 38 of receiver member 30. The outer dimension of bi-polar member 101 is preferably slightly smaller than the inner dimension of chamber 38 and lower portion 31b of central aperture 32 so that bi-polar member 101 is slidably and rotatably movable within chamber 38 and central aperture 32. Further, in the illustrated embodiment, the outer dimension of bi-polar member 101 is larger than the inner dimension of upper opening portion 31a, so that bi-polar member 101 cannot move into upper portion 31a of receiver member 30.

Figure 6A:
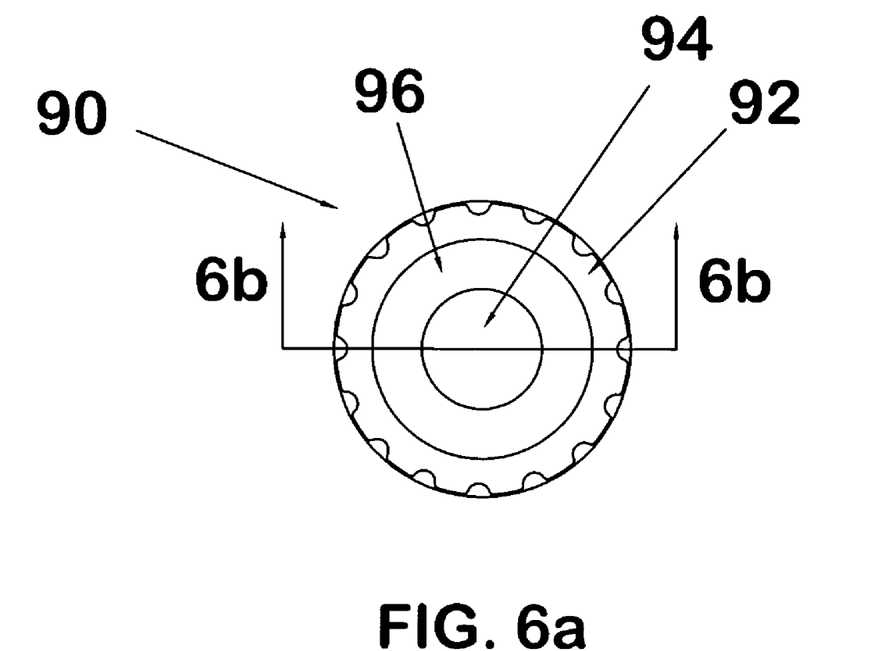
FIG. 6a is a top view of one embodiment of an internal threaded ring member that fits around the bone anchor and over the outer lower threaded portion in the receiver member to retain the internal saddle member and the bone anchor member used in the assembly illustrated in FIGS. 1 and 2.
Figure 6B:
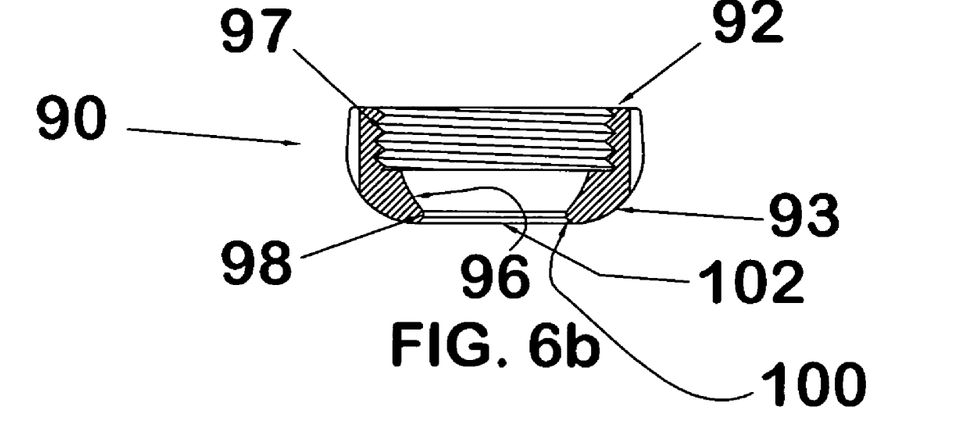

Referring now to FIGS. 6a-6b, there is shown one embodiment of an internal threaded ring member 90 in accordance with the teachings of the present invention. In the illustrated embodiment, internal threaded ring member 90 is a generally ring-shaped member with a central aperture 94. Internal threaded ring member 90 includes a top surface 92 and a bottom surface 93. An internal surface 96 of sidewall 98 substantially surrounds central aperture 94. In a lower portion of central aperture 94, internal surface 96 forms a portion of a sphere of radius substantially identical to the radius of head 54 of bone anchor 50 near bottom opening 102 of aperture 94. At bottom opening 102 the internal surface 96 is conical and angled outward at angle 100 to allow a greater range of angular positioning of bone anchor 50. In alternative embodiments, there may be single or multiple internal angles to the internal surface 96 in the lower portion of aperture 94 near bottom opening 102, such that internal surface 96 may have portions with a cylindrical, conical, spherical or of other appropriate configuration. The diameter of bottom opening 102 is smaller than the diameter of head 54 of bone anchor 50.

In an upper portion of central aperture 94, internal surface 96 may include threads 97 allowing for attachment to counterpart threads 41 proximate the lower end of receiver member 30.

Figures 7A, 7B, 7D:
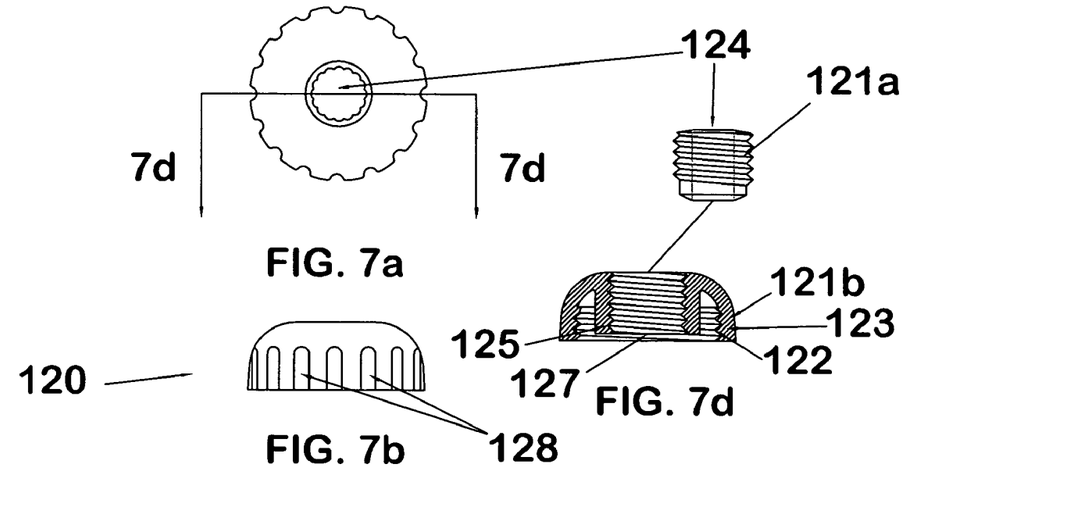
Figure 7C:
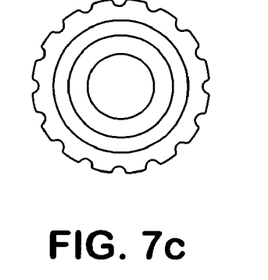

Turning to FIG. 7, there is shown one embodiment of a compression member assembly 120 for use in a system in accordance with the teachings of the present invention. In one embodiment, compression member 120, includes a set screw or plug 121 a having external threads and a print 124 for applying torque, and a nut-like cap 121b having internal threads 122 on an interior surface of an outer sidewall 123 and an inner sidewall 125 forming a threaded central socket 126 with an open bottom 127 for receiving plug 121b. Inner sidewall 125 forms a lower surface 129 adjacent open bottom 127, which may be planar. The outer surface of outer sidewall 123 may include a tool engaging print 128, such as slots for receiving a particular driver, or planar facets for interaction with a wrench. In one alternative embodiment, where receiver member 30 is internally threaded, nut-like cap 120 may be externally threaded on outer sidewall 123.

Generally referring to FIGS. 1, 2 and 9, assembly 20 may be assembled in the following manner: a bone anchor 50 may be inserted through a bi-polar member 101. An internal saddle member 70, the bone anchor 50 and bipolar member 101 may be inserted into a receiver member 30 through lower aperture 35. An internal threaded ring member 90 may then be place over bone anchor 50 and the bipolar member 101 and secured to the receiver member 30. This assembly may be performed as a series of individual steps or substantially in one step.

At this point, internal saddle member 70 remains slidably positioned in the interior surface of receiver member 30 and bi-polar member 101 and bone anchor 50 remain multi-axially moveable with respect to internal saddle member 70 and receiver member 30. Bone anchor 50, bi-polar member 101 and internal saddle member 70 are retained in receiver member 30 by internal threaded ring member 90. The head 54 of bone anchor 50 is supported between internal saddle member 70 and the bi-polar member 101, which is supported by internal surface 96 of internal threaded ring member 90.

Assembly 20 may be assembled to this point prior to use in a surgical procedure, although it will be appreciated that it may be assembled during the procedure. In using the embodiment of assembly 20, where bone anchor 50 is a bone screw, the bone anchor 50 may be threaded into an appropriately prepared hole in a bone (not shown). Threaded anchoring portion 52 may be inserted into the hole and an appropriate screwing tool used with tool-engaging print 60 to drive bone anchor 50 into the bone. It will be understood that in alternative embodiments of the invention, for example where bone anchor 50 is a bone hook, drilling a hole in bone and threading the anchor therein may not be necessary.

When bone anchor 50 is attached to a bone, receiver member 30 may be positioned so that bone anchor 50 forms a desired angle θ with the long axis of receiver member 30, as depicted in FIG. 1. The angle, θ, between bone anchor 50 and the long axis of receiver member 30 may be any value from about 0 to about 57 degrees in any direction up to a total of about 112 degrees total angulation. It will be seen that the maximum angle of bone anchor 50 relative to receiver 30 can be changed, for example by angling bone anchor 50 to its maximum in relation to the long axis of receiver member 30 and by angling bi-polar member 101 with respect to the long axis of receiver member 30. Typically, current pedicle screw system allow for up to approximately 20 to 30 degrees angulation (for a total angle of 40 to 60 degrees). In embodiments of systems in accordance with the present invention, similar angulation may be achieved by bone anchor 50 around a first spherical axis of rotation, with bi-polar member 101 adding from about 27 to about 37 additional degrees of angulation around a second spherical axis of rotation (for a total of approximately about 112 degrees total angulation).

As described above, receiver member 30 may be angled as the surgeon desires with respect to bone anchor 50. An elongated member, R such as a spinal rod, connector, or other orthopedic surgical implant, may be coupled to assembly 20. Elongated member R may be placed in U-shaped channel 45 of receiver member 30 (and transverse channel 75 of saddle member 70) and in contact with the interior surface of transverse channel 75. The nut-like cap 121b of a compression member 120 assembly may be threaded into/onto threads 44 of receiver member 30 the lower surface 129 of the inner sidewall 125 contacts the top edge of the internal saddle member 70.

As component 121b of compression member 120 is tightened, internal saddle member 70 is forced downward against bone anchor 50. Head 54 is thereby clamped between the bi-polar member 101 and the internal threaded ring member 90 and internal saddle member 70. In this way, bone anchor 50 may be locked into a desired angular position with respect to the remainder of assembly 20 (and elongated member R).

The set screw or plug 121a of a compression member 120 assembly, may be threaded into the threaded central sock 126 of the nutlike component 121b, passing through the open bottom thereof to contact the elongated member R. As component 121a of compression member 120 is tightened, elongated member R is forced downward against internal saddle member 70, which locks the elongated member R in place with respect to assembly 20 independently from the bone anchor 50.

Since each different component 121a and 121b of compression member 120 is separately tightened to compress different components, they generate apposing forces which lock the assembly, reducing the likelihood of involuntary loosening.

Preferred materials for constructing the various components of the present invention include stainless steel, titanium, and alloys containing the same. It will be recognized that any sturdy biocompatible material may be used to accomplish the osteosynthesis and other orthopedic surgical goals of the present invention.

While the present invention has been shown and described in terms of preferred embodiments thereof, it will be understood that this invention is not limited to any particular embodiment and that changes and modifications may be made without departing from the true spirit and scope of the invention as defined and desired to be protected.

What is claimed is:

1. An assembly for securing an elongated member for surgical stabilization of a bone, the assembly comprising:

a bone anchor comprising a bone engaging portion extending from a curvate head;

a bi-polar member, comprising a circular disc having a beveled exterior and an aperture extending from a top opening to a bottom opening;

a saddle member comprising a sidewall defining a center channel running from an upper edge to a lower opening and at least two paired branches defining an insertion channel running generally perpendicularly to the center channel, the center channel having an enlarged lower portion adjacent the lower opening sized to receive a portion of the head of an inserted bone anchor therein;

a receiver member comprising at least one sidewall defining a central channel passing from a first opening at a top end to a second opening at a bottom end, the central channel having an enlarged lower portion adjacent the bottom end sized to receive the saddle member and the bi-polar member with the head of an inserted bone anchor therein, and at least one transverse channel formed in an upper portion of the receiver member generally perpendicular to the central channel, the at least one transverse channel formed as two opposite slots extending from the top end of the receiver member;

a lower retaining member comprising a generally ring-shaped member having a central aperture with an upper opening at a top surface and a smaller lower opening at a lower surface and an attachment structure for attachment at a lower portion of the receiver member, wherein the lower opening and central aperture of the lower retaining member allow angular positioning of the bi-polar member with respect thereto until compression of the bipolar member between the lower retaining member and the curvate head of the bone anchor; and an upper retaining member comprising a cap having an outer sidewall and an inner sidewall, the outer sidewall configured for attachment to the upper portion of the receiver member and the inner sidewall forming a central socket with an open bottom.

2. The assembly of claim 1, wherein the bone engaging portion of the bone anchor comprises a threaded shaft.

3. The assembly of claim 1, wherein the curvate head of the bone anchor has a generally spherical shape.

4. The assembly of claim 1, wherein the curvate head of the bone anchor features a series of ridges or grooves.

5. The assembly of claim 1, wherein the enlarged lower portion of the center channel of the saddle member tapers from a narrower top to a wider bottom.

6. The assembly of claim 5, wherein the enlarged lower portion of the center channel of the saddle member has the shape of part of a sphere.

7. The assembly of claim 1, wherein the enlarged lower portion of the center channel of the saddle member has an interior surface with a friction or purchase enhancing surface configuration.

8. The assembly of claim 1, wherein an outer dimension of a lower portion of the internal saddle member is larger than an inner dimension of central channel in the upper portion of the receiver member.

9. The assembly of claim 1, wherein the beveled exterior of the bi-polar member has a generally spherical shape.

10. The assembly of claim 1, wherein the at least one portion of the beveled exterior of the bi-polar member has a roughened or knurled surface.

11. The assembly of claim 1, wherein the top opening of the bi-polar member has a greater diameter than the bottom opening of the bi-polar member such that the bone anchor may be inserted partially therethrough with the bone engaging portion passing out the bottom opening and the head of a bone anchor retained in the aperture adjacent at least open sidewall thereof.

12. The assembly of claim 1, wherein the receiver member further comprises an external threading disposed adjacent a bottom portion thereof for attachment to the lower retaining member.

13. The assembly of claim 12, wherein the attachment structure on the lower retaining member comprises an internal threading on a sidewall of the central aperture for interaction with the external threading on the bottom portion of the receiver member.

14. The assembly of claim 1, wherein the lower opening and central aperture of the lower retaining member allow angular positioning of the bi-polar member with respect thereto until compression of the bipolar member between the lower retaining member and the curvate head of the bone anchor when an elongated member is secured in the transverse channel.

15. The assembly of claim 1 wherein the central aperture of the lower retaining member has a concave surface for engaging an external surface of the bi-polar member.

16. The assembly of claim 1, wherein the receiver member further comprises an external threading disposed on the upper portion of the receiver member for attachment to the upper retaining member.

17. The assembly of claim 1, further comprising a set screw configured to attach to the central socket of the upper retaining member, passing out the open bottom to contact an elongated member in the at least one transverse channel.

18. The assembly of claim 1, wherein the bottom of the inner sidewall of the upper retaining member compresses against the upper edge of the saddle member upon installation to force the saddle member against the head of an inserted bone anchor, compressing the head of the inserted bone anchor against the bi-polar member and the bi-polar member against the lower retaining member to retain the bone anchor in a desired angular position.

19. A bone anchor system for securing a rod to a bone, the system comprising:
  a receiver having a body with an upper portion and a lower portion, a central channel passing from a first opening at a top end to a second opening at a bottom end, the central channel having a first width in the upper portion and a second width larger than the first width in the lower portion adjacent the bottom end, and a transverse channel formed in an upper portion by opposing slots extending from the top end of the receiver, the transverse channel being generally perpendicular to the central channel and a width sufficient to receive a spinal rod inserted therein;
  a receiver saddle comprising a sidewall defining a center channel running from an upper edge to a lower opening and at least two paired branches defining an insertion channel running generally perpendicularly to the center channel, the center channel having an enlarged lower portion adjacent the lower opening;
  a bi-polar disc comprising a circular body with a beveled exterior and an aperture extending from a top opening to a bottom opening, the top opening having a greater diameter than the bottom opening;
  a bone anchor comprising a bone engaging portion extending from a curvate head, the curvate head having a maximum width smaller than the top opening of the bi-polar disc and larger than the bottom opening of the bi-polar disc; and
  a lower retainer comprising a generally ring-shaped body with a central aperture and an attachment structure for attachment to the lower portion of the receiver, wherein the central aperture of the lower retainer allows angular positioning of the bi-polar disc with respect thereto until compression of the bi-polar disc between the lower retainer and the curvate head of the bone anchor.

20. The system of claim 19, further comprising an upper retainer comprising a cap having an outer sidewall and an inner sidewall, the outer sidewall configured for attachment to the upper portion of the receiver and the inner sidewall forming a central socket with an open bottom.

21. The system of claim 20, further comprising a generally cylindrical plug with external threading for attachment to an internal threading in the central socket of the upper retainer to thereby retain an inserted spinal rod in the transverse channel and insertion channel.

22. The system of claim 20, wherein the bottom of the inner sidewall of the upper retainer compresses against the upper edge of the receiver saddle upon installation to force the receiver saddle against the head of an inserted bone anchor, compressing the head of the inserted bone anchor against the bi-polar member and the bi-polar member against the lower retaining member to retain the bone anchor in a desired angular position.

23. The system of claim 19, wherein the beveled exterior of the bi-polar disc has a generally spherical curve corresponding to the generally spherical chamber of the central channel of the receiver.

24. The system of claim 19, wherein the aperture of the bi-polar disc is formed as a curved sidewall.

25. The system of claim 19, wherein the bone engaging portion of the bone anchor comprises a threaded shaft.

26. The system of claim 19, wherein the curvate head of the bone anchor has a generally spherical shape.

27. The system of claim 19, wherein the curvate head of the bone anchor has a series of ridges or grooves.

28. The system of claim 19, wherein a surface of the aperture and the beveled exterior surface of the bi-polar disc are roughened or knurled.

* * * * *